(12) United States Patent
Waiche (10) Patent No.: US 10,605,739 B2
(45) Date of Patent: Mar. 31, 2020

(54) DEVICE FOR MICROBIOLOGICAL ANALYSIS

(71) Applicant: EMD Millipore Corporation, Burlington, MA (US)

(72) Inventor: Gael Waiche, Molsheim (FR)

(73) Assignee: EMD Millipore Corporation, Burlington, MA (US)

( * ) Notice: Subject to any disclaimer, the term of this patent is extended or adjusted under 35 U.S.C. 154(b) by 0 days.

(21) Appl. No.: 13/756,570

(22) Filed: Feb. 1, 2013

(65) Prior Publication Data

US 2013/0143259 A1 Jun. 6, 2013

Related U.S. Application Data

(63) Continuation of application No. 12/584,807, filed on Sep. 11, 2009.

(30) Foreign Application Priority Data

Sep. 23, 2008 (FR) ..................................... 08 56407

(51) Int. Cl.
*G01N 21/64* (2006.01)
*G01N 21/76* (2006.01)
(Continued)

(52) U.S. Cl.
CPC ............. *G01N 21/763* (2013.01); *C12Q 1/04* (2013.01); *G01N 21/645* (2013.01);
(Continued)

(58) Field of Classification Search
CPC .......... G01J 3/4406; G01N 2021/6491; G01N 21/255; G01N 21/645; G01N 21/6447; G02B 21/22

See application file for complete search history.

(56) References Cited

U.S. PATENT DOCUMENTS 5,681,712 A 10/1997 Nelson
6,122,396 A * 9/2000 King et al. .................... 382/133
(Continued)

FOREIGN PATENT DOCUMENTS

EP 0753732 A2 1/1997
JP 9-281078 A 10/1997
(Continued)

OTHER PUBLICATIONS

Martin et al., "Light emitting diode microscope illumination for green fluorescent protein or fluorescein isothiocyanate epifluorescence", 2005, BioTechniques, vol. 38, No. 2, pp. 204-206.*
(Continued)

*Primary Examiner* — Jonathan M Hurst
(74) *Attorney, Agent, or Firm* — Nields, Lemack & Frame, LLC (57) ABSTRACT

The device for the microbiological analysis of a support adapted to contain microorganisms marked by a fluorophore agent, said agent being adapted to absorb light energy with an absorption spectrum (53) having a crest (53') at a predetermined absorption wavelength ($\lambda_2$) and to release that energy by emitting light with an emission spectrum (54) having a crest (54') at a predetermined emission wavelength ($\lambda_3$) distinct from said absorption wavelength ($\lambda_2$), comprises illuminating means; the spectrum (55) of the excitation light coming from the illuminating means having a crest (55') at a predetermined excitation wavelength ($\lambda_1$) with a predetermined difference between the excitation ($\lambda_1$) and absorption ($\lambda_2$) wavelengths by virtue of which it is made easy to discriminate the light emitted by said fluorophore agent from that coming from the illuminating means.

9 Claims, 5 Drawing Sheets

(51) Int. Cl.
*G01N 33/58* (2006.01)
*C12Q 1/04* (2006.01)

(52) U.S. Cl.
CPC ..... *G01N 21/6428* (2013.01); *G01N 21/6447* (2013.01); *G01N 33/582* (2013.01); *G01N 2021/6419* (2013.01); *G01N 2201/0627* (2013.01); *G01N 2201/0634* (2013.01)

(56) References Cited

U.S. PATENT DOCUMENTS

| | | | |
|---|---|---|---|
| 6,395,556 B1 * | 5/2002 | Lakowicz | G01N 21/6428 422/82.07 |
| 6,451,191 B1 * | 9/2002 | Bentsen | G01N 27/44791 204/600 |
| 6,509,166 B1 * | 1/2003 | Edberg | G01N 33/56961 435/4 |
| 6,825,930 B2 | 11/2004 | Cronin et al. | |
| 6,985,224 B2 * | 1/2006 | Hart | G01J 3/02 250/459.1 |
| 7,397,602 B2 | 7/2008 | Endo | |
| 2001/0038439 A1 * | 11/2001 | Doherty | A61B 3/0008 351/221 |
| 2003/0138353 A1 | 7/2003 | Bargoot et al. | |
| 2003/0214581 A1 | 11/2003 | Ikami | |
| 2004/0243318 A1 | 12/2004 | Ogawa et al. | |
| 2006/0024815 A1 * | 2/2006 | Allman et al. | 435/287.2 |
| 2006/0152721 A1 | 7/2006 | Korkeamaki et al. | |
| 2007/0153372 A1 | 7/2007 | Mazel | |
| 2009/0127475 A1 * | 5/2009 | De Lamberterie | G01N 21/6447 250/484.4 |
| 2010/0075408 A1 | 3/2010 | Waiche et al. | |
| 2010/0075409 A1 | 3/2010 | Waiche | |

FOREIGN PATENT DOCUMENTS

| | | |
|---|---|---|
| JP | 10-300672 A | 11/1998 |
| JP | 2000-316596 A | 11/2000 |
| JP | 2002-228663 A | 8/2002 |
| JP | 2003-532474 A | 11/2003 |
| JP | 2005-283322 A | 10/2005 |
| JP | 2006-512055 A | 4/2006 |
| JP | 2006-153888 A | 6/2006 |
| JP | 4029983 B2 | 1/2008 |
| JP | 2008-187935 A | 8/2008 |
| KR | 10-0753616 B1 | 8/2007 |
| WO | 01/85010 A2 | 11/2001 |
| WO | 02/061405 A2 | 8/2002 |
| WO | 2005/064318 A1 | 7/2005 |
| WO | 2006/077304 A1 | 7/2006 |
| WO | WO 2006/077304 * 7/2006 ............ G01N 21/64 |
| WO | 2006/119277 A2 | 11/2006 |
| WO | 2007/040459 A1 | 4/2007 |

OTHER PUBLICATIONS

Yang et al., Light-emitting-diode-induced fluorescence detector for capillary electrophoresis using optical fiber with spherical end, 2003, Talanta, 59, pp. 509-514.*

Nature Biotechnology, vol. 18, Nov. 2000, pp. 1191-1196, "Wavelength-shifting molecular beacons", TYAGI, et al.

Final Rejection dated May 15, 2013 in corresponding U.S. Appl. No. 12/584,807.

Final Rejection dated May 29, 2013 in co-pending U.S. Appl. No. 12/584,806.

Office Action dated Sep. 10, 2014 in corresponding U.S. Appl. No. 12/584,807.

Office Action dated Dec. 4, 2014 in co-pending U.S. Appl. No. 12/584,806.

French Search Report dated Jun. 17, 2009 in co-pending French Patent Application No. FR 0856405.

French Search Report dated Jun. 18, 2009 in corresponding French Patent Application No. FR 0856407.

Japanese Communication, with English translation, dated Oct. 4, 2011 in corresponding Japanese Patent Application No. JP 2009-212656.

Office Action-Restriction-dated Jun. 26, 2012 in corresponding U.S. Appl. No. 12/584,807.

Office Action dated Oct. 9, 2012 in corresponding U.S. Appl. No. 12/584,807.

Office Action-Restriction—dated Jun. 26, 2012 in co-pending U.S. Appl. No. 12/584,806.

Office Action dated Oct. 5, 2012 in co-pending U.S. Appl. No. 12/584,806.

Final Rejection dated Mar. 9, 2015 in corresponding U.S. Appl. No. 12/584,807.

Final Rejection dated Mar. 18, 2015 in co-pending U.S. Appl. No. 12/584,806.

Japanese communication, with English translation, dated Dec. 9, 2014 in corresponding Japanese patent application No. JP 2013-253509.

Japanese communication, with English translation, dated Jul. 3, 2012 in corresponding Japanese patent application No. JP 2009-212656.

Japanese communication, with English translation, dated Aug. 6, 2013 in corresponding Japanese patent application No. JP 2009-212656.

Applied and Environmental Microbiology, vol. 74, No. 16, Aug. 2008, p. 5068-5077, "Quantification of Target Molecules Needed To Detect Microorganisms by Fluorescence In Situ Hybridization (FISH) and Catalyzed Reporter Deposition-FISH", Hoshino, et al.

Cytometry Part A, 77A:623-634, 2010, "Viability States of Bacteria—Specific Mechanisms of Selected Probes", Strauber, et al.

Office action dated Jan. 27, 2016 in co-pending U.S. Appl. No. 12/584,806.

Final rejection dated Apr. 11, 2016 in co-pending U.S. Appl. No. 12/584,807.

Final rejection dated May 22, 2017 in co-pending U.S. Appl. No. 12/584,807.

Office action dated Sep. 28, 2016 in co-pending U.S. Appl. No. 12/584,807.

Final rejection dated Sep. 23, 2016 in co-pending U.S. Appl. No. 12/584,806.

Indian communication dated Feb. 16, 2017 in co-pending Indian patent application No. 1836/DEL/2009.

Office action dated Jul. 6, 2017 in co-pending U.S. Appl. No. 12/584,806.

Indian communication dated Mar. 17, 2017 in corresponding Indian patent application No. 1868/DEL/2009.

Final rejection dated Oct. 12, 2018 in co-pending U.S. Appl. No. 12/584,807.

Office action dated Sep. 25, 2018 in co-pending U.S. Appl. No. 12/584,806.

Office action dated Jan. 31, 2018 in co-pending U.S. Appl. No. 12/584,807.

Final rejection dated Jan. 22, 2018 in co-pending U.S. Appl. No. 12/584,806.

Office action dated Oct. 28, 2015 in co-pending U.S. Appl. No. 12/584,807.

Office action dated Jul. 2, 2019 in co-pending U.S. Appl. No. 12/584,807.

Notice of allowance dated May 30, 2019 in co-pending U.S. Appl. No. 12/584,806.

Notice of allowance dated Nov. 22, 2019 in co-pending U.S. Appl. No. 12/584,807.

* cited by examiner

DEVICE FOR MICROBIOLOGICAL ANALYSIS

This application is a continuation of Ser. No. 12/584,807 filed Sep. 11, 2009, which claims priority of French Application No. 0856407 field Sep. 23, 2008, the disclosures of which are incorporated herein by reference.

The present invention concerns a device for the microbiological analysis of supports that may contain microorganisms in order to detect the presence or absence of those microorganisms.

One way to analyze such supports consists of detecting the presence of the microorganisms by analysis of the fluorescence emitted by those microorganisms after they have been marked by what are referred to as flurogen or fluorophore markers.

These markers have the particularity of fluorescing only when they have been activated beforehand by an enzyme contained in the microorganisms.

These markers generally comprise a fluorophore group as well as a group capable of concealing or preventing the fluorescence of the fluorophore group from showing. When the microorganisms are present, the effect of the enzyme thereof is to modify that second group in order that the fluorescence of the first group may be detected.

Figure 7:
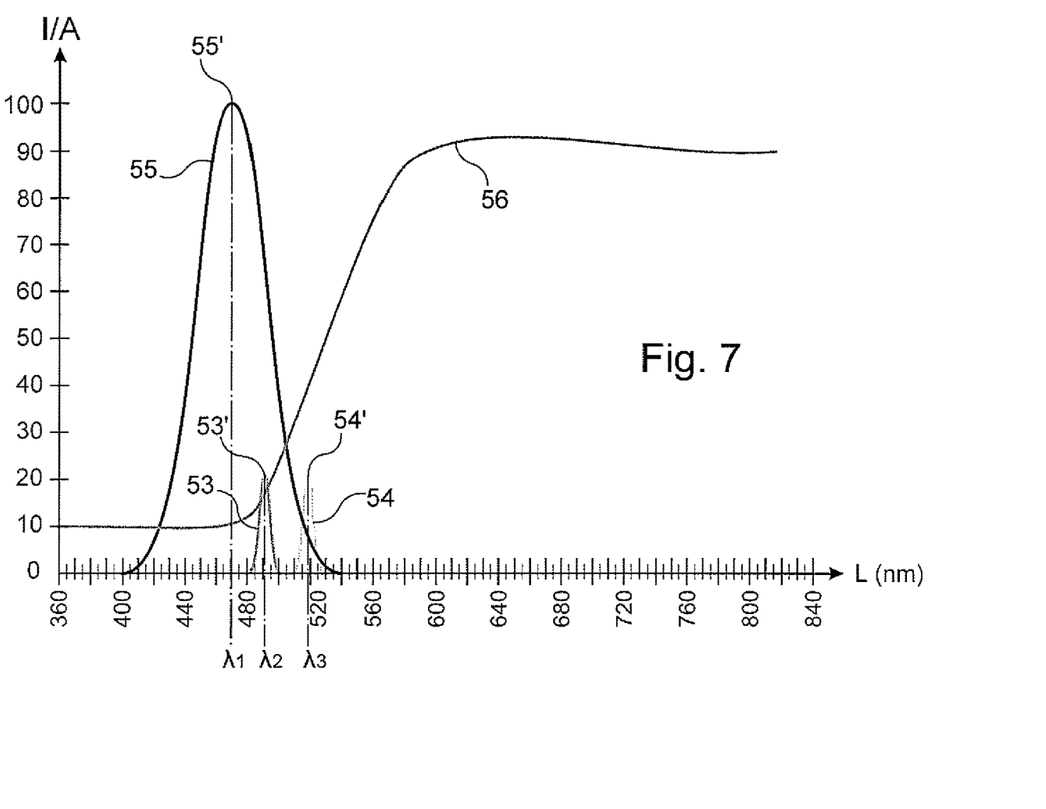
FIG. 7 illustrates the spectral diagrams of different optical members of a device according to the invention as well as the spectral diagram of the fluorophore agent used with that device to mark the microorganisms, with a common scale of wavelengths along the x-axis and a common scale of relative light intensity along the y-axis.

Thus, as illustrated by the spectra 53 and 54 of FIG. 7, when the microorganisms so marked are subjected to an appropriate excitation light, the fluorophore group is capable of absorbing light energy with an absorption spectrum 53 of which the crest 53' is at a wavelength $\lambda_2$ and of releasing that energy in the form of a characteristic fluorescent emission spectrum 54 of which the crest 54' is at a wavelength $\lambda_3$, distinct from $\lambda_2$.

Figure 9:
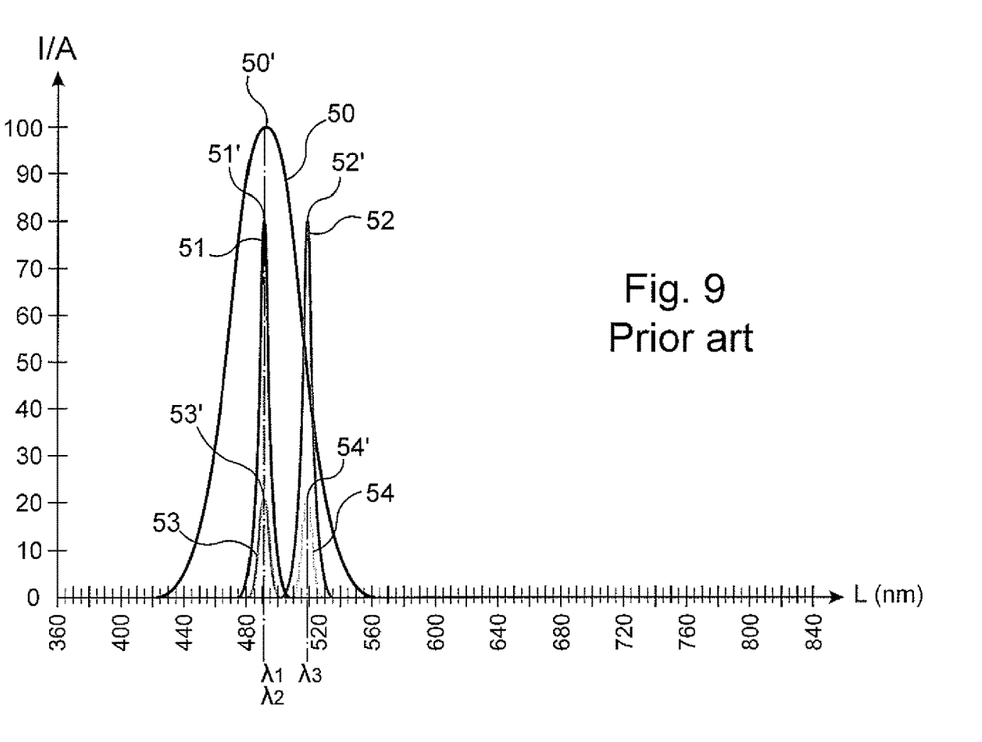
FIG. 9 illustrates spectral diagrams similar to those of FIG. 7 but for a device according to the prior art described previously.

For observing the fluorescence emitted by microorganisms in the presence of such markers, and as illustrated in FIG. 9, devices (integrated into microscopes) for microbiological analysis are already known comprising illuminating means for emitting the exciting light and of which the spectrum 50 of Gaussian distribution form has a crest 50' at a wavelength $\lambda_1$ that is chosen equal to the wavelength $\lambda_2$ to excite the fluorophore with sufficient energy in order for it to emit, in the presence of microorganisms, light with its emission spectrum 54.

Such a device is provided with an input filter, disposed between the illuminating means and the support to illuminate, such as band-pass filter of which the spectrum 51 is illustrated in FIG. 9, this filter having a very narrow passband centered on the wavelength $\lambda_1$ so as to select, given the wide spectral width of the illuminating means corresponding to the spectrum 50, only the wavelength that is useful to excite the fluorophore properly at the desired energy.

This device also comprises a filter disposed between the support to analyze and the zone for viewing the light coming from the support, the filter being illustrated by the spectrum 52 in FIG. 9 (here, a band-pass filter of narrow passband centered on the wavelength $\lambda_2$), in order only to let pass the light which is emitted by the fluorophore in response to the excitation light, filtered of all the other extraneous wavelengths.

Devices having such an arrangement are for example described in the U.S. Pat. No. 7,397,602.

The invention concerns the provision of a device for performing, like the device of the prior art, detection of fluorescence but which is both more economical and simpler while providing performance which is as good.

To that end it provides a device for the microbiological analysis of a support adapted to contain microorganisms marked by a fluorophore agent, said agent being adapted, on contact with said microorganisms, to absorb light energy with an absorption spectrum having a crest at a predetermined absorption wavelength ($\lambda_2$) and to release that energy by emitting fluorescent light with an emission spectrum having a crest at a predetermined emission wavelength ($\lambda_3$) distinct from said absorption wavelength ($\lambda_2$), said device comprising illuminating means adapted to illuminate said support in order for said marked microorganisms to emit, in response to the excitation light emitted by those illuminating means, light with said emission spectrum; characterized in that the spectrum of the excitation light coming from the illuminating means comprises a crest at a predetermined excitation wavelength ($\lambda_1$) distinct from said absorption ($\lambda_2$) and emission ($\lambda_3$) wavelengths of said fluorophore agent, such that said absorption wavelength ($\lambda_2$) is situated between said excitation ($\lambda_1$) and emission ($\lambda_3$) wavelengths with a predetermined difference between the excitation ($\lambda_1$) and absorption ($\lambda_2$) wavelengths, by virtue of which it is made easy to discriminate the light emitted by said fluorophore agent from that coming from the illuminating means.

The spectral offset between the crests of the excitation and absorption spectra with the absorption wavelength $\lambda_2$ which is thus situated between the excitation $\lambda_1$ and emission $\lambda_3$ wavelengths makes it possible advantageously to situate, between those absorption and emission wavelengths, the portion of the spectrum of the excitation light situated beyond $\lambda_1$ in order to obtain light having quite high energy at the wavelength $\lambda_2$ to excite the fluorophore such that it emits light by fluorescence and to have small overlap of the excitation spectrum with the emission spectrum at the wavelength $\lambda_3$ (and at neighboring wavelengths) in order that the light which comes from the illuminating means and which is reflected on the support to analyze does not cause significant parasitic interference with the light emitted by the fluorophore agent in the presence of microorganisms such that it is made easy to discriminate the light emitted by the fluorophore agent from that coming from the illuminating means.

More particularly, the overlap between the excitation spectrum and the emission spectrum thus being small by virtue of the spectral offset of the device according to the invention, the crest of the emission spectrum of the fluorophore is more detached from the crest of the spectrum of the excitation light and the ratio between the parasite energy at the emission wavelength of the fluorophore (coming from the light emitted by the illuminating means at that wavelength) and the energy actually coming from the fluorescence of the marked microorganisms is considerably improved.

It is thus possible to easily detect on the support the bright points corresponding to the marked microorganisms with sufficient contrast for them to be clearly observable, and in particular with the naked eye.

This spectral offset thus makes it possible, even for illuminating means having a non-negligible spectral dispersion (such as that illustrated by the spectra 50 and 55 in FIGS. 7 and 9), to dispense with having the input filter of the prior art devices without it being necessary nevertheless to replace such illuminating means by other illuminating means of which the spectral dispersion is lower (such as a laser for example, which is in general extremely costly).

This thus makes it possible to significantly reduce the manufacturing cost of such a device while minimizing the losses of light energy, since the presence of an input filter, in particular a filter with a narrow passband, necessarily leads to a substantial drop in energy throughput (and thus the quantity of light reaching the support to illuminate) for such a device.

As the light energy lost is less in the device according to the invention, it is thus possible, for the same electrical power consumed, to illuminate larger support surfaces to analyze (such as the surfaces of microporous filter membranes for example) than in the application to the microscope of the device of the prior art.

According to features that are preferred for reasons of simplicity and convenience for both manufacture and use:

said excitation wavelength ($\lambda_1$) is shorter than said absorption wavelength ($\lambda_2$), itself shorter than said emission wavelength ($\lambda_3$);

said spectrum of the excitation light comprises a peak of maximum light intensity centered on said excitation wavelength ($\lambda_1$);

the difference between said excitation ($\lambda_1$) and absorption ($\lambda_2$) wavelengths is less than the difference between said absorption ($\lambda_2$) and emission ($\lambda_3$) wavelengths of said fluorophore agent;

said device also comprises a window for viewing the light emitted by said fluorophore agent provided with a filter which is adapted to let the longest wavelengths pass and of which the cut-off wavelength is situated between said absorption wavelength ($\lambda_2$) and said emission wavelength ($\lambda_3$);

said illuminating means comprise at least one base on which is mounted at least one group of light sources, with said sources of that group being regularly spaced from each other to form an illuminating array for said support;

said illuminating means comprise two said bases inclined relative to each other in the direction of a predetermined location for reception of said support in the device;

each said base is inclined by an angle between 40° and 50° relative to said predetermined location for reception of said support;

said light sources are light emitting diodes; and/or said lighting means comprise a lamp adapted to emit polychromatic light and a filter adapted let pass the smallest wavelengths and of which the cut-off wavelength is situated between said absorption wavelength ($\lambda_2$) and said emission wavelength ($\lambda_3$).

The features and advantages of the invention will appear from the following description, given by way of preferred but non-limiting example, with reference to the accompanying drawings in which.

A description will now be given of a preferred embodiment of the device according to the invention with the help of FIGS. 1 to 5, before detailing its mode of operation with the help of the spectral diagrams illustrated in FIG. 7.

The device 1 illustrated in FIGS. 1 to 5 comprises a casing 2, illuminating means 3 formed from two illuminating members 4, a sliding drawer 5 and a viewing window 7.

Figure 2:
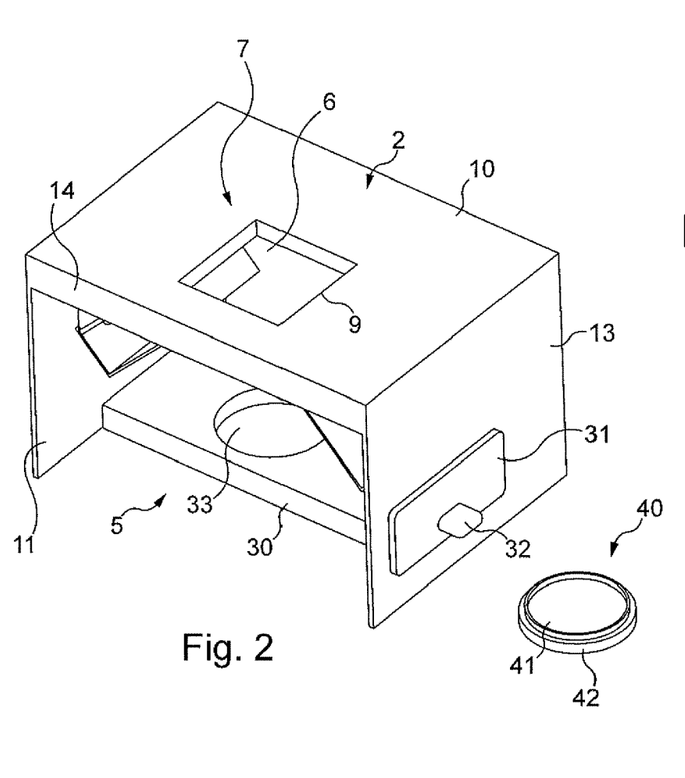
FIG. 2 is a perspective view of that device beside which is represented a filter unit to analyze in the device.

The casing is of parallelepiped general shape and has an upper wall 10 and four side walls 11 to 14, a portion of wall 14 being deliberately not shown in order to show the interior of the device.

The viewing window 7 is here constituted by a low-pass filter 6 (that is to say that it allows the lowest frequencies to pass, and thus the longest wavelengths), an opening 9 being formed in the upper wall 10 of the casing 2 to receive that filter 6 therein.

As will be seen below, the interior of this casing 2, delimited by the walls 10 to 14 and 30, forms an analysis chamber isolated from the surrounding light and in which the support to analyze is received.

The support to analyze is here a microporous membrane 41 belonging to a filter unit 40, here a unit commercialized by Millipore® under the trademark Milliflex®. This membrane 41 has a diameter of 55 mm and is surrounded by a body 42 of the filter unit.

The membrane 41 used here is of cellulose ester and has a pore size adapted to retain the microorganisms whose presence it is desired to detect, most often between 0.10 and 100 microns.

The drawer 5 has a body 30, a collar 31 and a grasping lug 32.

In the body 30 there is formed a cylindrical cavity 33 provided to receive a filter unit 40.

Figure 3:
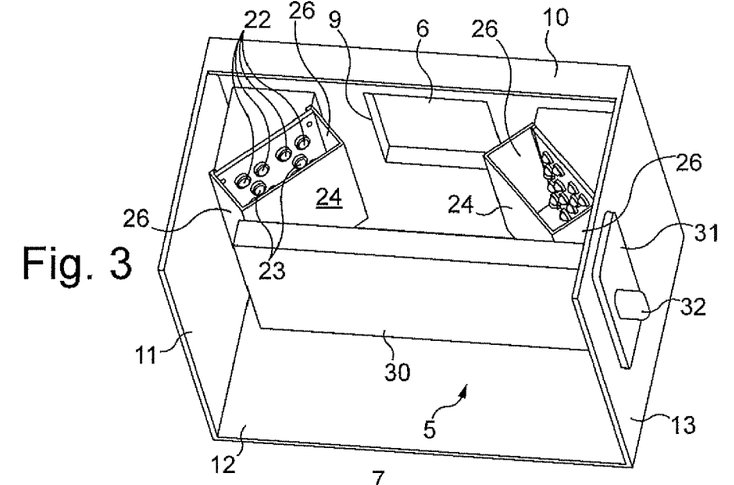
FIGS. 3 and 4 are respectively a perspective view taken from below and a section view in elevation taken on a median plane of symmetry of that device.
Figure 4:
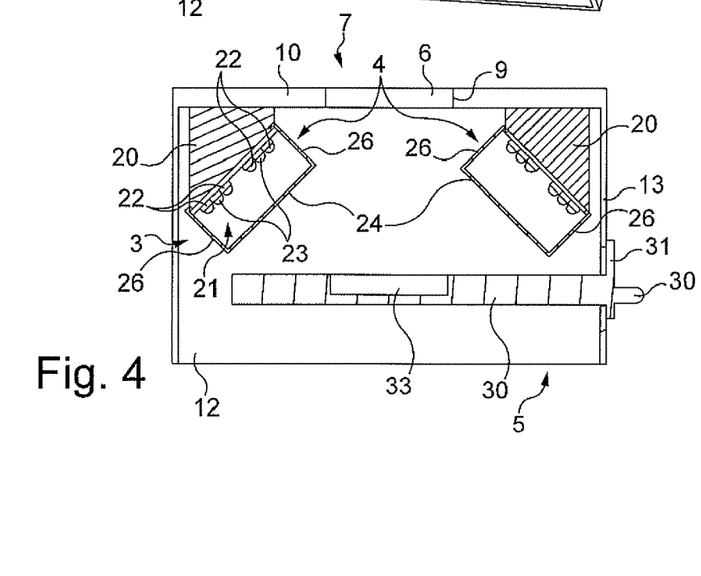

The illuminating means 3 will now be described with the help of FIGS. 3 to 5.

These means 3 comprise two separate illuminating members 4.

Each member 4 comprises a mounting 20 of trapezoidal section, a printed circuit board 21 on which two groups 27 and 28 of diodes 22 and 23 are disposed, a diffuser 24 covering those diodes and two black screens 26 between the edges of the board 21 and those of the diffuser 24.

The mountings 20 are fixed inside the casing 2 on the wall 10 of that casing, while the boards 21 are fixed to the mountings 20 on the inclined faces thereof, that are remote from those disposed against the wall 10 such that those boards are inclined towards each other in the direction of the reception zone 33 for the support 41.

Figure 1:
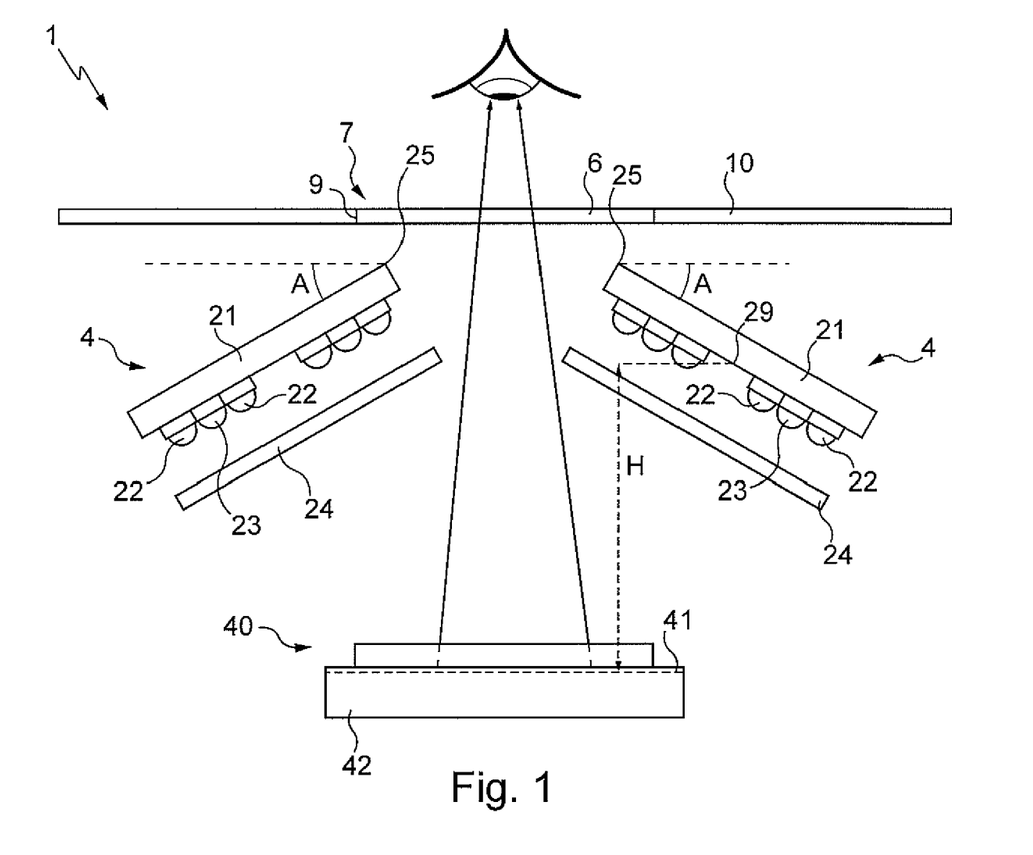
FIG. 1 is a diagram of a device according to the invention.

Each mounting 20 is thus provided such that each plate 21 has an inclination A (FIG. 1) of 45° relative to the wall 10 and to the predetermined location that the membrane 41 occupies, when the unit 40 is in the housing 33 of the device (FIG. 1).

The upper edges 25 of the boards 21 are at a distance from each other equal to 100 mm while those edges 25 are at a distance of 23 mm from the wall 10.

The summits of light emitting diodes 22 and 23 are situated at a distance of 15 mm from the diffusers 24.

These diffusers 24 are here made from a plate of glass on which one of the faces is sandblasted (the face which is turned towards the diodes).

Figure 5:
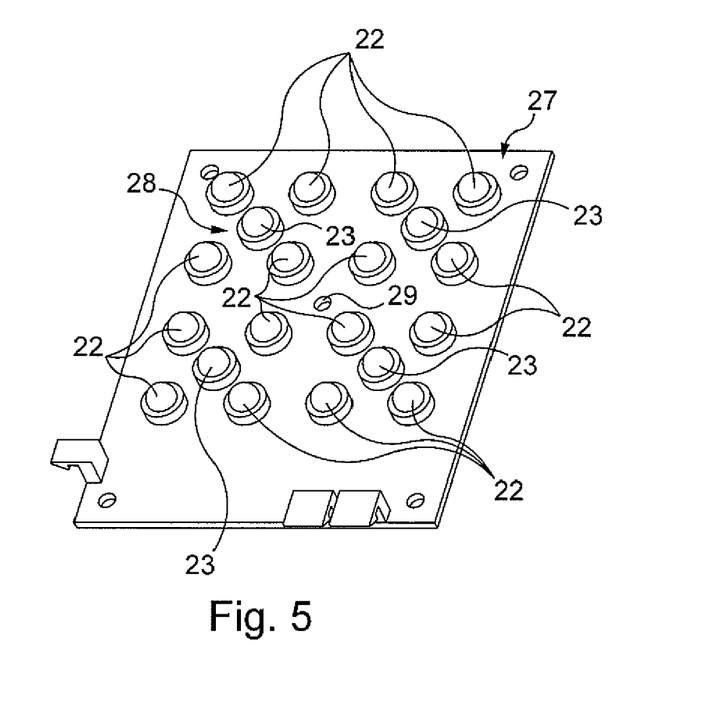
FIG. 5 is a perspective view of one of the two printed circuit boards of that device on which are fixed two groups of light emitting diodes, each emitting light at a predetermined wavelength.

On each printed circuit board, and as illustrated in FIG. 5, a first group 27 of diodes is disposed, constituted by sixteen diodes 22 as well as a second group 28 of diodes constituted by four diodes 23.

The diodes 22 are regularly spaced from each other and disposed in four equidistant rows of four diodes, such that each diode 22 is situated at a distance of 16 mm from the diodes 22 directly neighboring thereto. This group 27 thus forms an array of diodes making it possible to uniformly illuminate the membrane 41 when it is disposed in the casing 2 at its predetermined location, the center 29 of that array being situated at a height H of 54.75 mm from that predetermined location (FIG. 1).

The diodes 23 are distributed in the four corners of a square interlaced in the center of the array of diodes 22, each diode 23 being situated at a distance of 32 mm from the two diodes 23 neighboring thereto and at the center of a square at the corners of which are situated four diodes 22 (FIG. 5). The center of this array coincides with the center 29 of the array constituted by the diodes 22.

The diodes 22 are diodes from the company LUMILED© commercialized under the reference LXHL-PB01 and of which the emission spectrum 55 is illustrated in FIG. 7, this spectrum of Gaussian distribution form having a crest 55' at the wavelength $\lambda_1$ of 470 nm, thus emitting in blue.

The diodes 23 are diodes from the same company commercialized under the reference LXHL-PD01, of which the emission spectrum, not illustrated in the drawings, is also of Gaussian distribution form and has a crest at the wavelength of 625 nm thus emitting in red.

These diodes have a solid angle of emission of 140° for a relative intensity value of 25% and a solid angle of emission of 90° for a relative intensity value of 60%.

The diodes 23 have an emission power substantially four times greater than that of the diodes 22 such that they are four times less numerous than the diodes 22.

The arrays of diodes 22 and 23 are interlaced (that is to say nested within each other) so as to obtain the most homogenous light possible at the filter unit to be illuminated, whether the light comes from the diodes 22 or from the diodes 23.

Each group of diodes produces a light spectrum centered on a predetermined wavelength so as to be able to excite different predetermined types of fluorophore.

The conductive tracks on each board 21 are electrically linked to a command and control unit for the device (not shown).

The preparation of a sample to analyze will now briefly be described.

Prior to the actual detection step, the operator collects a sample to analyze (which may contain microorganisms) by filtration through a membrane 41 of a unit 40.

Once the microorganisms have been filtered and retained on the membrane, an optional step of growing the microorganisms in contact with an appropriate growth medium may be included. This growth medium is preferably a gel medium on which the membrane is deposited after filtration. This step, which is optional, enables colonies of each of the microorganisms initially filtered to be obtained, which increases the number of cells to detect.

The membrane and the microorganisms that it contains are then placed in contact with a composition for rendering the walls of the microorganisms permeable and the fluorophore markers are then incorporated into the permeable-rendering composition in order to enter the inside of the microorganisms to detect.

A description will now be given of the implementation of the determination of the presence or absence of microorganisms on a sample so prepared on the basis of the device according to the invention.

In a first phase, the drawer 5 is pulled and the operator places a filter unit 40 (which may possibly be covered by a transparent cover not illustrated to protect the membrane from exterior contamination) in the cavity 33 of that drawer. The drawer 5 is then pushed until the collar 31 abuts the wall 13 such that the membrane 41 is disposed in its predetermined location within the casing 2 in order to be illuminated.

Depending on the fluorophore which was used to mark the microorganisms, the operator next selects (for example via a switch not illustrated in the drawings) the corresponding diodes 22 or 23 to turn on (the diodes 22 in the example illustrated) so as to uniformly illuminate the whole of the surface of the membrane 41 and to excite, at the right wavelength, the fluorophore that served for the marking.

The diffusers 24 as well as the spatial distribution of the diodes on the boards 21 make it possible to have a particularly homogenous illumination of the whole surface of the membrane 41, whatever the group of diodes used.

As the boards 21 are disposed one on each side of the opening 9 receiving the filter 6, the light coming from the filter unit 40 which is emitted in response to the excitation light from the diodes passes through that filter as illustrated in FIG. 1 such that it is possible to observe the light response of the membrane 41 through the filter 6, with the naked eye or else via a camera.

The light response obtained in the presence of microorganisms using the different spectral diagrams illustrated in FIG. 7 will now be detailed.

In FIG. 7, the spectrum 55 is of Gaussian form and corresponds to the spectrum of the excitation light (here the spectrum produced by the diodes 22) and which has a peak of which the crest 55' corresponding to the maximum light intensity value is at the wavelength $\lambda_1$ equal to 470 nm.

The spectra 53 and 54 respectively correspond to the absorption spectrum and to the emission spectrum of the fluorophore chosen here to mark the microorganisms present on the membrane.

The fluorophore represented here is 5-6 CFDA (Carboxy-Fluorescein-Di-Acetate).

The absorption spectrum 53 has a crest 53' at the wavelength $\lambda_2$ greater than $\lambda_1$ and the emission spectrum 54 has a crest 54' at the wavelength $\lambda_3$ greater than $\lambda_2$.

In the example illustrated $\lambda_2$ is equal to 492 nm and $\lambda_3$ to 517 nm, the difference between $\lambda_1$ and $\lambda_2$ here being less than the difference between $\lambda_2$ and $\lambda_3$.

The excitation wavelength $\lambda_1$ is deliberately chosen to be less than $\lambda_2$ such that the crest 55' of the spectrum 55 is offset relative to the crest 53' of the spectrum 53, on the opposite side to the spectrum 54. This offset is chosen in order for the light coming from the illuminating means to have sufficient energy to excite the fluorophore without that light causing significant parasitic interference with that emitted by the fluorophore in response to that excitation light.

The spectrum 56 is that of the filter 6 of the viewing window, it cut-off frequency being chosen (here of the order of 550 nm) to let through essentially the light emitted by the fluorophore (spectrum 54) and to stop the light at shorter wavelengths, in particular those coming from the diodes 22 after reflection on the unit 40.

This output filter (a colored filter) is weakly selective to allow a sufficient quantity of light to return to the eyes of the user giving a generally bright scene and which is thus comfortable to observe while ensuring a level of contrast which is adapted for observation with the naked eye.

When the excitation light coming from the illuminating means 3 illuminates the membrane 41 of the filter unit 40, each location of that membrane having microorganisms marked by the fluorophore is rendered visible in the form of a bright spot of small size (a few hundreds of microns) directly observable with the naked eye coming out of the filter 6.

The values of the angle A and of the height H provide an optimum rendering for the reading of the bright spots on the membrane 41, whether with the naked eye or via a camera.

These values have been determined by applying a black mark and a fluorescent yellow mark to a control membrane and by seeking, for different values of that angle A and of that height H, the configurations A, H for which the brightness of the fluorescent band is maximum while minimizing the parasitic brightness on the black mark.

It has thus surprisingly proved that the range [40°-50°] for the angle A gave both a maximum light intensity for the fluorescent mark and practically an absence of parasite light for the black mark, which thus corresponds to an optimum in terms of reading comfort.

So as to have a certain safety margin relative to the play in mounting the device it is thus the average value of 45° which has been chosen here.

As regards the height value H, this is a function of the size of the object to illuminate, the different configurations tested have shown that for a membrane of a diameter of 55 mm and for a value range for the angle A between 40° and 50°, the best results were obtained for a height range between 39.75 and 69.75 mm. Similarly here, it is the average value of 54.75 mm which was chosen in this example.

The device is also adapted, by adjusting the height H, to illuminate types of sample other that membranes, and generally any support adapted to contain microorganisms (whether on a surface or in a volume) and whose presence it is desired to detect by fluorescence.

Figure 6:
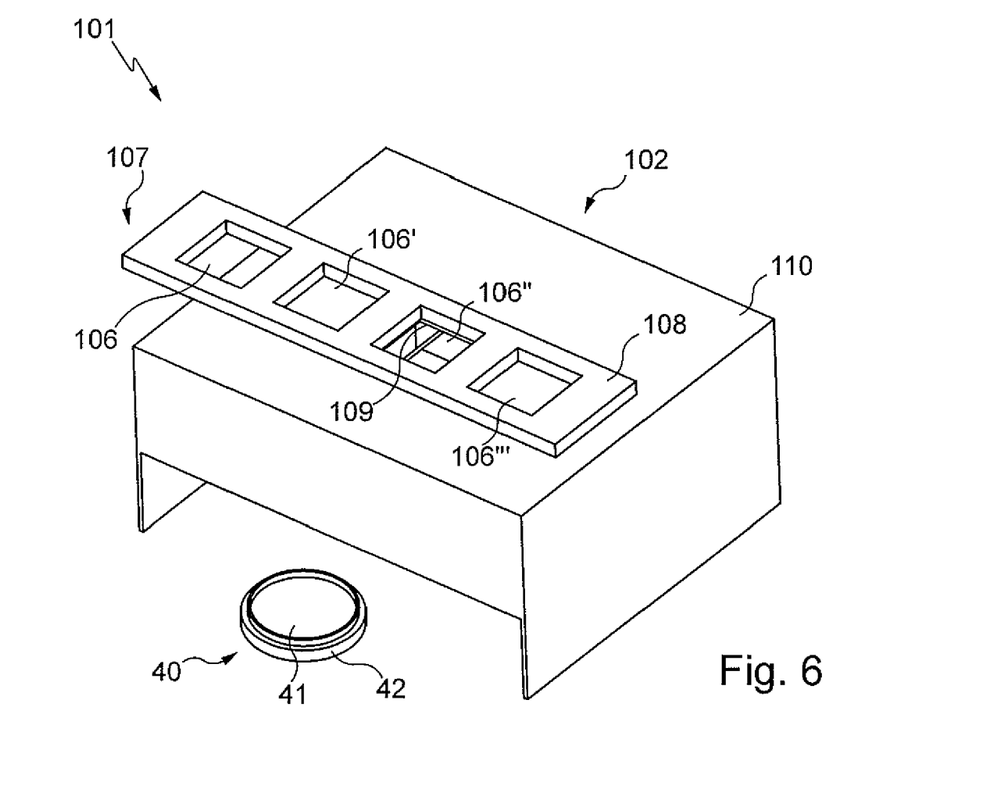
FIG. 6 is a perspective view of another embodiment of the device according to the invention.

Another embodiment of this device is represented in FIG. 6.

Generally speaking, the same reference numbers increased by 100 are used for similar parts.

The device 101 has the same features as the device 1 apart from it lacking the drawer 5 (the filter unit 40 here being directly placed on a table for example) and for the fact that the viewing window 107 is here formed from a slide 108 of rectangular form disposed against the wall 110 of the casing 102 and from four filters 106 to 106''', each of the filters being housed in a corresponding opening of the slide 108.

Each optical filter is a low-pass filter, thus allowing the low frequencies to pass (the longest wavelengths) and of which the cut-off frequency is distinct from the other cut-off frequencies.

The slide 108 is engaged in a guide rail (not illustrated) of that device so as to be able to place any chosen one of the four filters 106 to 106''' in register with the opening 109 of the wall 110.

It is thus possible, depending on the fluorophore chosen and on the diodes which are turned on, to select from the four available filters the one which has the most adapted cut-off frequency (to obtain the best contrast for example).

In one embodiment not illustrated, the filter 6 is not a low-pass filter but a band-pass filter of which the passband is centered on the wavelength $\lambda_2$.

Figure 8:
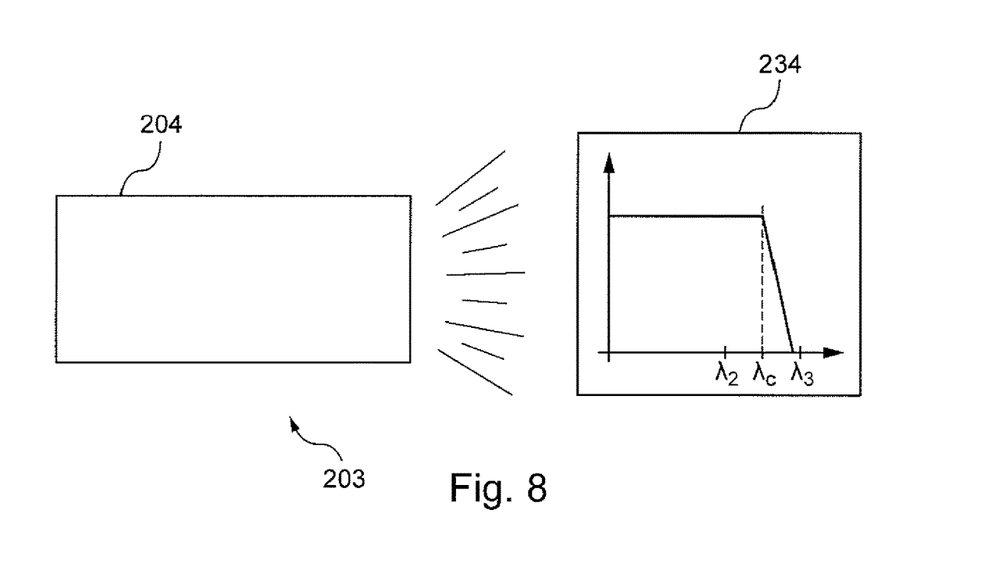
FIG. 8 is a diagram of a part of still another embodiment of the device according to the invention.

In still another embodiment illustrated diagrammatically in FIG. 8, the crest of the spectrum of the illuminating means does not necessarily have to be localized and thus extends over a larger range of wavelengths by using for example as illuminating means 203, instead of the diodes, a lamp 204 of polychromatic light associated with a high-pass filter 234 adapted allow the highest frequencies to pass, that is to say the shortest wavelengths, which is less costly than the band-pass filter of the prior art and of which the cut-off wavelength $\lambda_c$ is situated between the absorption wavelength $\lambda_2$ and the emission wavelength $\lambda_3$ (FIG. 8).

Lastly, it will be noted that such an illuminating system may also be produced in different versions for many other applications such as analysis by microscope, scanning of biochips, reading of plates by fluorescence, cytometry, transilluminators, PCR real-time reading, the geometrical configuration of the device for each of these applications then being in a version specific to the application in question. The frame of the device to which the bases 21 are fixed is not necessarily a casing like the casing 2 illustrated; it may for example be a hoop surrounding the optics of a microscope.

The present invention is not limited to the embodiments described and represented, but encompasses any variant form thereof.

The invention claimed is:

1. A method for the microbiological analysis of a support containing microorganisms marked by a fluorophore agent positioned in an interior of a casing forming an analysis chamber isolated from surrounding light, the analysis chamber comprising a drawer having a body, a collar, and a grasping lug, wherein in the body there is formed a cylindrical cavity provided to receive a filter unit, the filter unit comprising a microporous membrane as a support, said agent absorbing light energy on contact with said microorganisms with an absorption spectrum having a crest at a predetermined absorption wavelength $\lambda 2$ and releasing that energy by emitting fluorescent light with an emission spectrum having a crest at a predetermined emission wavelength $\lambda 3$ distinct from said absorption wavelength $\lambda 2$, said method comprising illuminating said support with excitation light from light emitting diodes positioned in said interior of said casing in order for said marked microorganisms to emit, in response to said excitation light, light with said emission spectrum; wherein the spectrum of said excitation light comprises a crest at a predetermined excitation wavelength $\lambda 1$ distinct from said absorption $\lambda 2$ and said emission $\lambda 3$ wavelengths of said fluorophore agent, such that said absorption wavelength $\lambda 2$ is situated between said excitation $\lambda 1$ and emission $\lambda 3$ wavelengths with a predetermined difference between the excitation $\lambda 1$ and absorption $\lambda 2$ wavelengths, by virtue of which the light emitted by said fluorophore agent passes through a low-pass colored filter and is then viewed by a naked eye of a viewer through a window formed in said casing and provided with said low-pass colored filter, said low-pass colored filter being the only filter between said support and the naked eye of the viewer, and the light emitted by said fluorophore agent and that coming from said excitation light is discriminated by the naked eye of the viewer in the surrounding light, without the use of an input filter, wherein said light emitting diodes and said window are arranged such that said microorganism contained on said support faces both said light emitting diodes and said window.

2. The method according to claim 1, wherein said excitation wavelength $\lambda 1$ is shorter than said absorption wavelength $\lambda 2$, itself shorter than said emission wavelength $\lambda 3$.

3. The method according to claim 1, wherein said spectrum of said excitation light comprises a peak of maximum light intensity centered on said excitation wavelength $\lambda 1$.

4. The method according to claim 1, wherein the difference between said excitation $\lambda 1$ and absorption $\lambda 2$ wavelengths is less than the difference between said absorption $\lambda 2$ and emission $\lambda 3$ wavelengths of said fluorophore agent.

5. The method according to claim 1, wherein a cut-off wavelength of said low-pass colored filter is situated between said absorption wavelength $\lambda 2$ and said emission wavelength $\lambda 3$.

6. The method according to claim 1, wherein said support is illuminated with an illuminating member comprising at least one base on which is mounted at least one group of light sources, with said sources of that group being regularly spaced from each other to form an illuminating array for said support.

7. The method according to claim 6, wherein said illuminating member further comprises two bases inclined relative to each other in the direction of a predetermined location for reception of said support in the device.

8. The method according to claim 7, wherein each said base is inclined by an angle (A) between 40° and 50° relative to said predetermined location for reception of said support.

9. The method according to claim 1, wherein said casing has an outer wall, and wherein prior to said illuminating step, said drawer is pulled from said casing, said support is placed in said cavity, and said drawer is pushed back into said casing until said collar abuts said outer wall of said casing.

* * * * *